United States Patent [19]

Thompson

[11] Patent Number: 5,240,414
[45] Date of Patent: Aug. 31, 1993

[54] METHOD FOR SHADE SELECTION IN RESTORATIVE DENTISTRY

[76] Inventor: Charles C. Thompson, Rt. 4, Box 30, Ellisville, Miss. 39437

[21] Appl. No.: 855

[22] Filed: Jan. 5, 1993

[51] Int. Cl.⁵ .............................. A61C 19/10
[52] U.S. Cl. ........................................ 433/26
[58] Field of Search ........................ 433/26; 356/421

[56] References Cited

U.S. PATENT DOCUMENTS

| | | | |
|---|---|---|---|
| 4,523,852 | 6/1985 | Bauer | 356/421 |
| 4,654,794 | 3/1987 | O'Brien | 433/26 |
| 4,657,399 | 4/1987 | Hall | 433/26 |
| 4,793,805 | 12/1988 | Pitre | 433/26 |
| 4,802,850 | 2/1989 | Boon | 433/26 |
| 4,810,193 | 3/1989 | Wieder | 433/26 |

FOREIGN PATENT DOCUMENTS 169093 10/1951 Austria .................................. 433/26

Primary Examiner—John J. Wilson
Attorney, Agent, or Firm—David H. Semmes

[57] ABSTRACT

A process and apparatus for simulated color reproduction as applied to dental prosthesis, viz.: crown bridge restoration, including the charting of hue, chroma, value and translucency wherein there is implemented a three part shade guide consisting of forty-two pieces representing respectively opacity, body and enamel laminates, selectively interacted to present chromatic combinations.

3 Claims, 1 Drawing Sheet

METHOD FOR SHADE SELECTION IN RESTORATIVE DENTISTRY

BACKGROUND OF THE INVENTION

In the field of Restorative Dentistry significant advances have been made in recent years, particularly in the area of porcelain to metal restorations. The dental ceramist, with the modern dental porcelains and wide range of metal alloys may now create a porcelain to metal restoration that effectively duplicates appearance, color and vitality of the surrounding natural dentition.

However, one aspect of creating this porcelain to metal restoration has not enjoyed significant advances or changes since its inception. That aspect is the composite proper interpretation of the natural tooth color to be duplicated, that correct color being simultaneously communicated accurately to the dental ceramist. It is the norm rather than the exception that the color is misinterpreted by the dentist, the reason being that he does not have at his disposal a wide and varied selection of colors from which to select.

In practice, the standard shade selection guide used by most dentists consists of a kit comprising sixteen shade tabs, each with a handle. Respective shade tabs being defined as a piece of porcelain or plastic, formed to the shape of an anterior tooth. Each such tab presents one numbered color image.

Currently, these sixteen tabs have been divided into four basic color groups. The groups are: reddish-brown, five tabs; reddish-yellow four tabs; grey four tabs and reddish-grey three tabs.

The practitioner dentist would select one of the tabs and place it for comparison next to the patient's natural tooth. A careful side-by-side observation would dictate whether this tab closely simulates the color of the natural tooth. If the tab does not match, then this same trial and error procedure would be repeated with numerous other tabs. After the best color match had been selected, then the number and letter denoting the selected tab was communicated to the dental ceramist. The ceramist would then rely upon that letter and number code to select the correct porcelain powders to be used for construction of the restoration itself, that would match that particular color.

In natural dentition there are many more colors and combinations of colors that appear then in this standard shade guide. One may observe that from this very limited number of colors to choose from, it would be very difficult to properly select a given color that would match reasonably close to the natural dentition; yet each day a multitude of dentists attempt to select correct tooth color by using this very limited color selecting resource. This can be and very often is a frustrating experience for the dentist and dental ceramist. This very experience of proper selection of natural tooth color and accurate communication of this selection to the dental ceramist is what is addressed by the present invention, defined as Custom Pre-formed Shade Selection System, hereinafter CPSSS.

Among the reasons why proper color selection is rendered so difficult with the system in use today, one must be conversant with color terminology. Likewise, understanding the professional terms will allow us very easily to comprehend how the CPSSS addresses and resolves the difficulties discussed. These terms will be used interchangeably to define minor art difficulties and will also be used to describe the solutions.

COLOR TERMS: Named, defined with examples.

(A) Hue: The name that identifies the color; for example red, green, yellow blue, etc. Hue may also be a combination of colors, for example: reddish-yellow, reddish-brown, etc.

(B) Chroma: The strength, intensity or saturation of the hue. For example, an avocado is deep green, displaying a high chroma. On the other hand a green apple is light green, displaying a low chroma.

(C) Value: The brightness of any color measured and understood to be in the range of white to black. Any point in between white and black will naturally comprise a certain intensity of grey. For example, one part white paint mixed with three parts black paint would yield dark grey paint. Dark grey constitutes a low value; on the other hand, one part black paint mixed with three parts white paint would result in a light grey paint, constituting a high value.

(D) Translucency: The range from transparent to opaque. For example, a glass of water is transparent; a glass of milk is opaque and a glass of water with two drops of milk stirred is translucent.

The above four terms define the color components found individually in varying degrees and cooperatively in varying ratios in every tooth color. Whereas an elementary understanding of these terms is somewhat easy, nonetheless a proper interpretation and accurate communication of the varying degrees and ratios is much more difficult. For example, each time the color is selected by the dentist he/she must select the proper hue—reddish-brown, reddish-yellow, etc. Then the chroma must be determined, that being the intensity of the hue. Next, one must determine the value of the color, which is the brightness or the amount of grey present in the color. Last, one must describe how translucent the tooth is.

THE PRIOR ART

In accordance with the prior art process using the standard shade guide, a handle is attached to a color tab that is made of porcelain and shaped like a front tooth. There is an enamel layer of porcelain to which is affixed the dentine layer thereof. The two layers of porcelain being then fused together are supposed to represent a three layer porcelain restoration. Unfortunately, the actual porcelain used to make the tab is not the same kind of porcelain that is used to make the porcelain restoration which desirably has three distinct layers. By adopting this standard shade selection system, the shade tab itself has only two layers as opposed to the three that significantly exist in the porcelain restoration system hereinafter defined. Moreover, that system the dentine layer was much too thick and there was no opaque layer. Unfortunately also, the porcelain used in the two layer tab was not the same porcelain used in the present three layer porcelain restoration; thus the person selecting the color has only 16 predetermined combinations of hue, chroma, value and translucency to choose from. Among the more significant prior art patents are the following: Robert Bauer, U.S. Pat. No. 4,523,852 entitled Color Comparison Reference Standard; John K. O'Brien, U.S. Pat. No. 4,654,794 entitled Methods of Determining the Proper Coloring for a Tooth Replica.

SUMMARY OF INVENTION

In accordance with the invention, the most important step in the color selection process is developing a correct description of the value or brightness. If this is incorrectly determined, even with correct hue, chroma, and translucency, the color will either appear too dark or too light in the mouth. Either one would be a failure. It has often been found that the value of the desired color is also the most difficult aspect of the process to correctly determine. Accordingly, this task of correct color selection is quite complex and certainly no simple procedure when performed thoroughly.

Briefly the invention is stated to be: In the process of color reproduction as applied to dental prostheses, viz: crown bridge restoration, the charting of hue, chroma, value and translucency, including the implementation of a three-part shade guide wherein 42 pieces representing opacity, body and enamel layers are selectively interacted to present chromatic combinations.

Having previously defined the terms used in the trade, there follows the application of steps in proper order to determine most accurately a given tooth color.

IN THE DRAWINGS

Figure 5A:
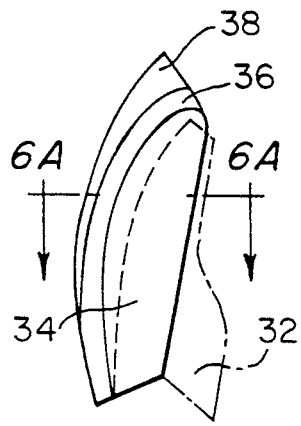
FIGS. 5A and 5B are schematic lateral view of the CPSSS shade tab of the invention hereunder, FIG. 5B being an exploded view of FIG. 5A.
Figure 5B:
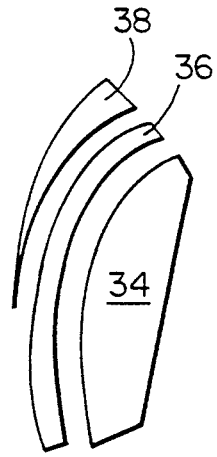
Figure 6A:
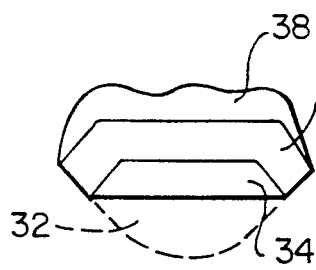
Figure 6B:
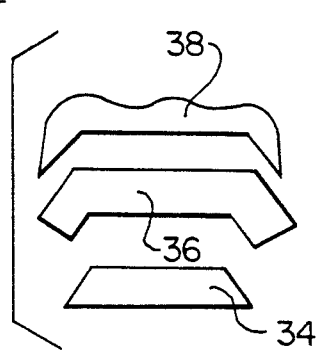

FIGS. 6A and 6B, where FIG. 6A is an incisal view of the tab of FIGS. 5A taken along the lines 6A—6A of FIG. 5A, FIG. 6B being an exploded view of FIG. 6A.

Figure 7:
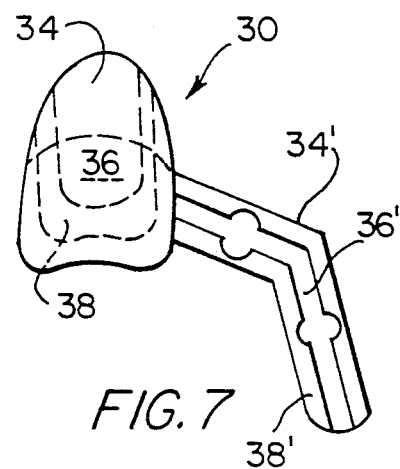

FIG. 7 is a view in front elevation of a completely assembled CPSSS shade tab.

DESCRIPTION OF THE PREFERRED EMBODIMENTS

Figure 1:
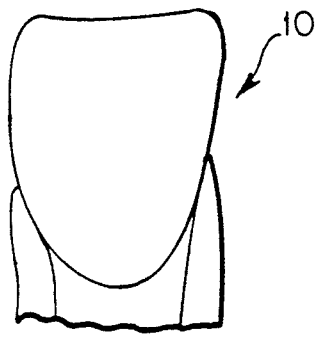
FIG. 1 is a view in front elevation of an upper anterior tooth.
Figure 2:
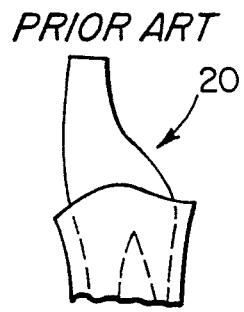
FIG. 2 is a view in side elevation of the tooth depicted in FIG. 1 following preparation for porcelain to metal restoration.
Figure 3:
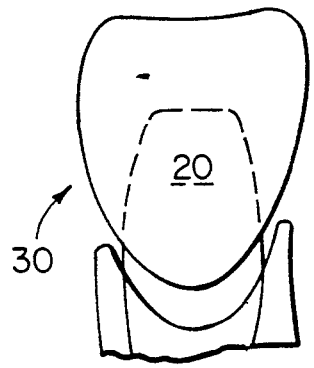
FIG. 3 is a view in front elevation of the partially restored tooth of FIGS. 1 and 2.
Figure 4:
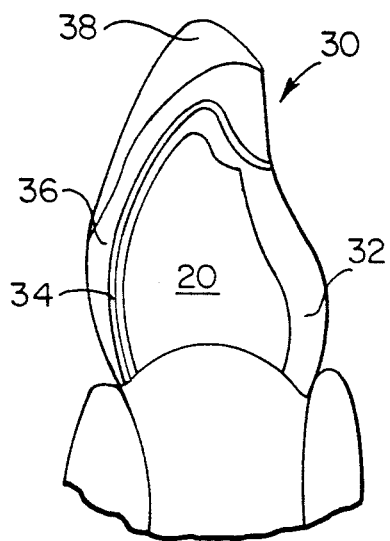
FIG. 4 is a view in vertical section of a typical porcelain to metal restoration and its component parts.

By way of background FIGS. 1-3 inclusive indicate the prior art mode of porcelain to metal restoration. FIG. 1 showing a front view of upper anterior tooth 10, precedent to preparation for reception of a porcelain to metal restoration, reference tooth 20 FIG. 2 In FIG. 3, the porcelain to metal restoration of the invention has been effected as at 30, a porcelain restoration being applied.

Referring to FIG. 4-7 inclusive, there are four component parts that comprise the current porcelain to metal restoration 30, namely metal understructure or matrix 32 to which the dental porcelain is fused. Among the three different layers of dental porcelain that make up the ceramic composite of the restoration are respectively, the opaque layer of porcelain 34, the dentine layer 36, and enamel layer 38. The opaque layer is defined primarily in terms translucency and value. Translucency herein is deemed to be opaque, on the opposite end of the spectrum from transparency. The effect of this opacity is to mask out the metal matrix 32 whereas, the value of this layer 34 contributes initially to the overall brightness or darkness of the color. Actually, this layer 34 comprises a pre-determined intensity of grey with a small amount of color pigment incorporated therein.

Dentine layer 36, the middle layer of porcelain contributes substantially exclusively to the color of the restoration and it being defined primarily by the terms hue, chroma and translucency, wherein as to hue the groups are reddish-brown, reddish-yellow, grey and reddish-grey. As to chroma, when applied to the dentine layer, the intensity of the colors presented are light, medium and dark pigmentations. Again, translucency hereunder as opposed to transparency consists of sufficient clarity for the grey of the opaque layer 34 to cast its effect on the color pigmentation of the dentine layer 36.

Finally, the enamel layer 38 is semi-transparent with varying amounts of blue and grey pigmentation, thereby contributing to the overall value and translucency of the color, per se.

Referring to FIGS. 5, 5a, 6 and 6a unlike the known prior art, the entire CPSSS herein is constructed with the very same porcelain that is used to make the porcelain restoration itself. Reference is made to drawings 5A,-5B wherein the CPSSS shade tab is depicted, absent the complete metal restoration of FIG. 4. In FIGS. 5A-5B and 6A-6B, the prepared matrix of the original tooth is depicted in phantom. FIGS. 5A-B and 6A-B show the respective laminates to be fusion connected. In actuality, these comprise vertical sectional views comparable to the sectional view of the completely restored tooth of FIG. 4. FIGS. 6A and 6B are incisal views of the tab, elements 34, 36, 38 being connected in FIG. 6 and disconnected in FIG. 6B, an exploded view of the shade tab.

The CPSSS tab thus consists of three precise interconnecting pieces of porcelain, namely 34, 36 and 38. Each layer represented will be the ideal shape and thickness that would be found in the actual porcelain restoration, excepting opaque layer 34. In the complete restoration hereunder, that layer 34 is nominally 0.2 mm in thickness but in the construction of the tab it will be of increased thickness. This increased thickness of the opaque layer does not change its effect on the desired color.

Referring to FIG. 7, a complete assembly of the tab 30 is shown, Here enamel tab 38 overlaps elements 36 and 34 of the CPSSS tab, per se. Appropriate interconnecting handles 34', 36' and 38' permit super position of the pieces forming the tab, after the application of a thin film of glycerin which has been applied to both sides of the middle layer 36. Such a minute connecting medium will ensure proper light transmission. In the method, the three layers 34-36-38 of porcelain having been connected, the dentist in less than one minute will have constructed a simulated custom, pre-formed porcelain-to-metal restoration, lacking the metal, per se. One may now compare the guide 30 to the color of the existing natural dentition.

In the CPSSS method there are sixteen opaque tabs 34, sixteen dentine tabs 36 and fourteen enamel tabs 38, each of said tabs in their own order being adapted to precise interconnection with others. Thus the standard guide aforesaid, provides the dentist with sixteen color combinations from which to select. Accordingly, the method and apparatus provide the dentist a total of 3,584 color combinations from which to choose thus reducing the possibility of misinterpreting the correct color matching for porcelain-to-metal restorations. Ideally, the respective porcelain members 34-36-38 of the invention are contained in their respective holders, separated into their own color groups and lettered and numbered accordingly.

The dental operator scans the natural dentition with the entire dentine tab holder approximately two inches in front of the mouth. One or more of these tabs may appear to match the color closely. The operator would take the number of tabs out of the holder and place each of them individually next to the natural tooth. An observation is made and the same procedure is repeated with the remaining tabs. Finally, the most appropriate dentine tab 36 is selected. The predetermined usual opaque tab 34 and enamel tab 38 to be used with this dentine tab 36 is numerically identified on the dentine handle 36' along with an identity letter and number of the opaque tab 34 and enamel tab 38. The identified opaque tab 34 is inserted into its place, and these tabs 34-36 are now observed together. If the color still looks good, then the identified enamel tab 38 is affixed. The shade would be written to the dental ceramist this way (ORB3-DRB3-E3).

Here follows an example of when the predetermined opaque and enamel layers are not correct The dentine tab of DRY3 is determined to be correct by the operator, but the value is lower than predetermined ORY3 and E3 display. The options are: any of the other opaque and enamel tabs 34-36 that have a lower value. The same principle can work in reverse. If the DRY3 is correct and the ORY3 and E3 display value too low, the options are any of the other opaque and enamel tabs that have a higher value.

The CPSSS is easy to learn and use. With the use of this system a more accurate color combination is determined and communicated to the dental ceramist. This provides the dental ceramist with a more detailed description of the desired color than the standard shade guide currently used.

The invention is defined herein with specific reference to the ensuing claims.

I claim:

1. A method of custom pre-formed shade selection in dental porcelain-to-metal restoration wherein plural shade tabs are employed to simulate color reproduction and/or tooth shade, the method comprising:
    A) first selecting an opaque porcelain laminate tab having preselected translucency and value characteristics;
    B) secondly selecting and interfitting upon the opaque laminate, a dentine porcelain laminate tab having preselected hue, chroma and translucency characteristics;
    third-selecting and interfitting an enamel porcelain laminate tab of preselected semi-transpartent characteristic, contributing to the overall value and translucency externally of the dentine porcelain laminate;
    D) comparing a resulted color reproduction of interfitted laminates to the tooth to be restored.

2. The method of claim 1 wherein the respective porcelain laminates are fabricated of the same porcelain composition as the actual porcelain to metal restoration.

3. The method of either claims 1 or 2 wherein the available opaque tabs are 16 in number, the definite tabs are 16 in number and the enamel tabs are 14 in number, comprising together 3,584 combinations.

* * * * *